United States Patent [19]
Coons et al.

[11] Patent Number: 4,806,476
[45] Date of Patent: Feb. 21, 1989

[54] EFFICIENT CELL FUSION PROCESS

[75] Inventors: Teresa Coons, Albuquerque, N. Mex.; Barry Avner, Franklin, Tenn.

[73] Assignee: Lovelace Medical Foundation, Albuquerque, N. Mex.

[21] Appl. No.: 765,866

[22] Filed: Aug. 13, 1985

Related U.S. Application Data

[63] Continuation-in-part of Ser. No. 521,196, Sep. 8, 1983, abandoned, which is a continuation-in-part of Ser. No. 406,823, Aug. 10, 1982, abandoned.

[51] Int. Cl.$^4$ .................. C12N 15/00; C12N 5/02; C12N 5/00; C12R 1/91
[52] U.S. Cl. .................. 435/172.2; 435/172.3; 435/240.26; 435/240.27; 435/948; 935/99; 935/100; 935/101; 935/109
[58] Field of Search .................. 435/172.2, 240, 68, 435/241, 948, 172.3; 935/93, 100

[56] References Cited

U.S. PATENT DOCUMENTS

| | | | |
|---|---|---|---|
| 4,159,988 | 7/1979 | Eibl et al. | 935/93 |
| 4,262,090 | 4/1981 | Colby, Jr. et al. | 435/68 |
| 4,394,448 | 7/1983 | Szoka, Jr. et al. | 435/320 |
| 4,451,570 | 5/1984 | Royston et al. | 435/240 |
| 4,621,053 | 11/1986 | Sugimoto | 435/68 |
| 4,642,291 | 2/1987 | Cairncross et al. | 435/68 |

OTHER PUBLICATIONS

Fournier, Proc. Natl. Acad. Sci. USA 78(10), pp. 6349–6353 (1981).
ATCC Catalogue 5th ed., 1985, p. 133.
Hoffman, Proc. Natl. Acad. Sci. USA 77(2), pp. 1139–1143 (1980).
Hope et al, Biochemical Society Transactions 5, pp. 1144–1146 (1977).
Schneiderman et al, Somatic Cell Genetics 5(2), pp. 363–369 (1975).
Mercer et al, "Techniques for Decreasing the Toxicity of Polyethylene Glycol", Techniques in Somatic Cell Genetics, ed. Shay (1982), pp. 23–34.
Eisen, Immunology, Harper and Row, Publishers, Philadelphia (1982), pp. 510, 515 and 516.
M. D. Scharff et al, "Hybridomas as a Source of Antibodies", Hospital Practice, Jan. 1981, 60–66.
G. H. Littman et al, "Production of Human B-Cell Hybridomas from Patients with SLE", Arth. Rheum, 25; No. 4 (Suppl): 528 (1982).
D. Papahadjopoulos et al, "Fusion of Mammalian Cells by Unilamellar Lipid Vesicles: Influence of Lipid Surface Charge, Fluidity and Cholesterol", Biochemical et Biophysica Acta, 323:23–42 (1973).
R. C. MacDonald et al, "Interactions between Lipid Vesicles and Cell Membranes", Annals. N.Y. Acad. Sci., 1978, 308:200–214.
F. J. Martin & R. C. MacDonald, "Lipid Vesicle-Cell Interactions—II Induction of Cell Fusion", The Journal of Cell Biology, 90:506–514 (1976).
D. Papahadjopoulos and A. Portis, "Calcium-Induced Lipid Phase Transitions and Membrane Fusion", Ann. N.Y. Acad. Sci., 308:50–66 (1978).
G. Poste and A. C. Allison, "Membrane Fusion", Biochimica et Biophysica Acta, 300:421–465 (1973).
M. A. Alspaugh et al, "Antibodies to Cellular Antigens in Sjogren's Syndrome", J. of Clinical Investigation, vol. 55, May 1975, 1067–1073.

Primary Examiner—John Edward Tarcza
Attorney, Agent, or Firm—Nilsson, Robbins, Dalgarn, Berliner, Carson & Wurst

[57] ABSTRACT

Cell fusion is induced between tumor cells that do not secrete a desired protein and mammalian cells or microcells derived from mammalian cells which secrete the desired protein, by substantially removing at least calcium ions to destabilize the cell membranes, adding a fusogen to the destabilized cells, and then adding back polyvalent cations.

11 Claims, 2 Drawing Sheets

EFFICIENT CELL FUSION PROCESS

CROSS-REFERENCE TO RELATED APPLICATIONS

This application is a continuation-in-part of application Ser. No. 521,196, filed Sept. 8, 1983, entitled EFFICIENT HYBRIDOMA FUSION, which is a continuation-in-part of application Ser. No. 4,206,823, filed Aug. 10, 1982, entitled EFFICIENT HYBRIDOMA FUSION, both now abandoned.

BACKGROUND AND SUMMARY OF THE INVENTION

The routine production of monoclonal antibodies relies on the fusion, or hybridization, of tumor cells, such as myeloma cells or virus-transformed cells and antibody secreting cells, such as those found in spleen or peripheral blood. The resulting hybridoma produces the specific antibodies of the blood or spleen cell parent while retaining the longevity in culture, and tumor-forming ability in animals, of the tumor cell parent. The procedure suffers from a number of limitations primarily arising from the fact that the tumor cell line must be a mutant line having certain characteristics which are only rarely found.

One requirement is that the tumor cells do not secrete infectious virus, so that the antibodies can be used with safety in treating patients. It would also be desirable, although with modern separation methods not critical (as will be exemplified), to select a tumor line that does not secrete immunoglobulins.

Another limitation arises from the requirement with present procedures that there be a method for selecting the hybridoma cells away from unfused tumor cells. As reported by M. D. Scharff et al. in "Hybridomas as a Source of Antibodies", *Hospital Practice*, Jan. 1981, 61-11, only about one out of every 200,000 spleen cells actually forms a viable hybrid with a myeloma cell. Accordingly, the unfused cell and the myelomamyeloma hybrids must be selectively eliminated (there is no need to eliminate unfused spleen cells because they die out in culture and are rapidly overgrown by the hybrids), which is usually accomplished by culturing the tissue cells in HAT (hypoxanthine, aminopterin and thymidine) medium. The myeloma or tumor cells are selected so as to lack HGPRT (hypoxanthine guanine phosphoribosyl transferase), and/or thymidine kinase (TK), enzymes the cell requires in order to use exogenous hypoxanthine and thymidine to synthesize purines. Cells lacking HGPRT and/or TK die when grown in the presence of aminopterin, which blocks endogenous synthesis of purines. Myeloma or tumor cells that have been fused to spleen or peripheral blood cells containing HGPRT and TK are able to use the hypoxanthine and thymidine in the HAT medium and therefore survive. Accordingly, the HAT solution is utilized as a means to select the fused cells from the background of unfused and nonhybridoma cells. In order to obtain a tumor cell line that is deficient in HGPRT and/or TK, one must select the tumor cells for azaguanine, thioguanine or bromodeoxyuridine resistance. Those cells containing HGPRT and TK enzymes take up the toxic nucleotide analogs during culturing and die, while the resistant cells survive. Thus, the tumor line must be one which not only does not secrete infectious virus, and preferably one which does not secrete immunoglobulins, but it must also be azaguanine, thioguanine or bromodeoxyuridine resistant (i.e., selectable in HAT medium).

There are significant reasons for requiring HAT selectability related to the fact that fusion rates are generally low, as indicated by Scharff et al. supra; because of a limited number of successful fusions, the culture is quickly overrun by unfused tumor cells. The low rate of fusion results at least in part from the fact that the standard fusion agent, polyethylene glycol (PEG), is in fact relatively toxic to cells. Methods not involving the use of an enzyme deficient tumor line are known. Recently, there has been reported the use of diethylpyrocarbonate to pretreat tumor cells. Unfused tumor cells treated with diethylpyrocarbonate will die. However, diethylpyrocarbonate itself is quite toxic to the fused cells, resulting in a very low rate of fusion, "Production of Human B-Cell Hybridomas from Patients with SLE", Littman et al., *Arth. Rheum.* 25; No 4 (Suppl.): 528 (1982). Other researchers have successfully used lipid vesicles for intratype fusion. See, in this regard, D. Papahadjopoulas et al., "Fusion of Mammalian Cells by Unilamelar Lipid Vesicles: Influence of Lipid Surface Charge, Fluidity and Cholesterol", *Biochimica et Biophysica Acta*, 323:23-42 (1973); R. C. McDonald et al., "Interactions Between Lipid Vesicles and Cell Membranes", *Ann. N.Y. Acad. Sci.*, 308: 200-214 (1978); and F. J. Martin et al., "Lipid Vesicle-cell Interactions—II. Induction of Cell Fusion", *The Journal of Cell Biology*, 70:506-514 (1976). Such researchers have concluded that successful lipid bridged fusion in vitro depends strongly upon calcium ion-induced phase changes. (See F. J. Martin et al., supra, and D. Papahadjopoulos et al., "Calcium-Induced Lipid Phase Transitions and Membrane Fusion", *Ann. N.Y. Acad. Sci.*, 308:50-66 (1978).)

On the other hand, G. Poste et al., "Membrane Fusion", Biochimica et *Biochysica Acta*, 300:421-45 (1973), attempt to describe what they perceived as a natural mechanism for cell fusion during a large number of cellular and subcellular activities. In referring to natural intratype in vivo cell fusions, key importance is attributed to the displacement of calcium ions from the cell membranes. The authors also indicate that cholesterol plays an adverse role in restricting phospholipids, thus inhibiting cell fusion.

In general, the fusion agent of choice in the creating of hybridomas has been PEG, and in all standard lymphocyte fusion procedures various concentrations and/or molecular weights of PEG are used as the fusing agent. During the first hours and days after fusion, the critical period when hybridized cells are in danger of being overgrown by unfused tumor cells, the hybrids are at a distinct disadvantage. It is for this reason that a means for selecting against the tumor cells has been required. If it were possible to avoid the toxic effect of PEG and still achieve fusion, "selectable" tumor lines would not necessarily be needed.

Another reason for low fusion rates lies in the fact that the mutant tumor lines, selected for HAT sensitivity, very often have poor inherent fusion rates. Despite several years of work by a number of investigators, only several selectable fusion lines are available, none of which actually works very well. On the other hand, if the line did not have to be HAT selectable, a large and variable group of useful tumor lines would be immediately available for use.

The present application is directed to a procedure which does not rely upon a HAT selectable tumor line by avoiding the use of PEG in the fusion process. Rather, a more physiological approach has been taken involving a plurality of steps that results in destabilization of the target cell membranes, the formation of bridges between the cells, and cell fusion. Even though Poste et al., supra, have described the natural in vivo mechanism of cell fusion as including displacement of calcium ions from the membranes, when prior workers, such as Papahadjopoulas et al., supra, have attempted to fuse cells of the same type in vitro using phospholipid vesicles, they have had to increase the presence of calcium ions; depletion has been contraindicated. In contrast, we have discovered that in order to achieve intertype fusion in vitro using a fusogen such as a phospholipid, one must substantially remove at least calcium ions, to destabilize the cell membranes; thereafter polyvalent ions, such as calcium ions, are added back.

The procedure of the present invention is efficient and quick, resulting in viable and rapidly dividing hybridized cells after as short a period as 24 hours. When using a nonselectable tumor line as the fusion partner, no overgrowth of hybrids is found due to the extremely rapid growth of the hybrid cells. Accordingly, the hybridized cells can readily be separated from tumor cells present in the same cultures by limiting dilution cloning, i.e., cultures are diluted to a concentration allowing theoretical distribution of one cell per tissue culture well. All cells subsequently arising in that well have the same parent and are genetically identical.

In one embodiment, a chelating agent is added to a mixture of tumor cells and cells which secrete a desired endogenous protein or other desired biologically active substance, to substantially remove at least calcium ions, preferably ions of both calcium and magnesium, from the cell environment, whereby to destabilize the membranes of the cells. Alternatively, calcium and magnesium ions may be substantially removed by repeatedly washing the cells in the fusion mixture with calcium and magesium-free medium, i.e., by repeated centrifugations and resuspensions in the described medium.

In another embodiment, microcells containing one to ten chromosomes are produced from cells having the capacity to produce the desired biologically active substance and mixed with the tumor cells. In this embodiment, removal of calcium ions or calcium and magnesium ions destabilizes the tumor cells, following which microcells are treated to remove divalent cations. The microcells and tumor cells must be treated separately because of the need for different modes of centrifugation occasioned by the difference in size between microcells and tumor cells. The microcells are produced by a process which includes the steps of blocking the growth of the cells in the metaphase stage, disrupting the nuclear membrane and reforming a membrane around one to ten chromosomes.

A fusogen, for example, a phosphoglyceride, is added to the destabilized cells or mixture of destabilized tumor cells and microcells and then polyvalent cations, including calcium ions, are added back to the mixture of fusogen and destabilized cells or fusogen, destabilized tumor cells and microcells, whereby to obtain fused cells, such as hybridomas or microcell transerted tumor cells.

It will be appreciated that the fusion procedure of this invention has broad application and can be used to fuse cells that produce metabolites other than antibodies. In broader concept, many other cell types and many forms of microcells can be "immortalized" by fusion with appropriate tumors, making the commercial preparation of such proteins as interferons, hormones, and the like vastly more efficient. By using the present procedure, hybridoma technology can be used to produce materials that are otherwise producible only with the techniques of recombinant DNA. In its broader form, with the cells secreting their own natural product, albeit in an indefinite unregulated manner, the process of reaching commercial production levels would be quicker and easier. Candidates for fusion are readily obtainable since time and effort would not be required to search for suitable "selectable" tumor mutants, but presently available tumor lines can be immediately used.

In accordance with this broader statement of the present invention, we provide a method for preparing fused cells that produce, for example, endogenous proteins such as antibodies, interferons, lymphokines, hormone precursors, hormones or other biologically active substances. Insulin, growth hormone, L-thyroxin, estradiol, testosterone, hydroxycortisone and cortisol are only a few examples of such substances. The process entails mixing together (a) first, tumor cells that do not produce, for example, endogenous proteins of the selected type; and (b) second, mammalian cells that are capable of producing the selected protein or microcells produced from such cells. Usually the second cells are non-tumor mammalian cells but a tumor-tumor hybridoma will also be illustrated.

Calcium and magnesium ions are substantially removed from the cell environment, either by chelation or by repeated washing, whereby to destabilize the membranes of the cells. A fusogen is added to the destabilized cells and then polyvalent cations are added back to the mixture of fusogen and destabilized cells, whereby to obtain by fusion hybridomas of the tumor cells and non-tumor cells or microcell transerted tumor cells. Finally the hybridomas or microcell transerted tumor cells are reproduced by standard cloning procedures.

DETAILED DESCRIPTION

Figure 1:
FIG. 1 is a photograph at 100× magnification of cells from a microtiter well 18 hours after a standard PEG fusion procedure, typical in appearance of cultures for at least 48 hours after fusion with PEG.

The following description will provide details specifically for the production of human monoclonal antibodies. The same procedure applies in other contexts, for example, for the production of mouse monoclonals, simply by substituting spleen cells for peripheral blood. In this regard, because good fusion lines (HAT-sensitive) are available in the mouse system, the major advantage of utilizing the present invention in producing mouse monoclonals is economic. Because the present invention avoids the use of, and therefore the toxicity of, PEG, there is a drastic decrease in the time expnditure required to produce a desired antibody and fewer tries are needed to get the right antibodies, because fusion efficiency and growth success are generally better with cells fused by the present method. As indicated above, the present procedure can be used with a much broader range of cell types than those producing antibodies. The procedure is directly applicable, simply by substitution of the cell type, to mammalian eucaryotic cells capable of producing a wide variety of biologically active substances. In certain instances it may be desirable to fuse antibody-secreting lymphocytes from one mammalian species with a tumor cell line from a closely related species, thus producing an interspecies hybridoma. The same procedure applies.

In the preparation of human monoclonal antibodies, for example, we can start with peripheral blood lymphocytes, which can be from a normal patient or from one suffering from a disease such that the blood contains significant levels of antibodies. For example, one can use peripheral blood lymphocytes from a patient suffering from any one of the autoimmune diseases, such as the rheumatic diseases of systemic lupus erythematosis (SLE), rheumatoid arthritis, mixed connective tissue disease (MCTD) or scleroderma. If desired, cells from other human tissues, such as human pituitary cells, may be used.

In order to increase the chances that specific antibody-secreting cells will fuse with a tumor cell, we stimulate the lymphocytes with the appropriate antigen in vitro prior to fusion. This is not a new step in and of itself. In vitro immunization procedures are necessary for the production of specific human antibodies, since one cannot with safety immunize humans directly to produce antibodies of interest. However, even when the blood sample is from a patient suffering from one or more of the autoimmune diseases, it is nevertheless preferred to stimulate the lymphocyte, since, in accordance with the present process, such stimulation makes normal cells more likely to fuse, perhaps because, unlike spleen cells from immunized mice, human peripheral blood lymphocytes are not at a maturation stage optimal for fusion. The in vitro stimulation procedure induces maturation of the lymphocytes and may cause their cell membranes to become less stable and "sticky", so that the cells are more likely to fuse when brought into contact with other cells or microcells under appropriate conditions. According to the present procedure, in vitro stimulation thus accomplishes two purposes: (1) clones of cells capable of secreting the desired antibody are preferentially expanded, thus increasing the number of these cells available for fusion with the tumor cell; and (2) the cells are "activiated" so that they are more susceptible to the fusing agents. The specific antigen used to stimulate the lymphocytes, the antigenic activator, will, of course, depend upon the desired nature of the antibodies. In addition to the specific antigen, a non-specific activator can be used. Such activators, called polyclonal lymphocyte activators, are well known, exemplified by such materials as pokeweed mitogen, lipopolysaccharides, Concanavalin A and phytohemagglutinin.

Procedurally, the peripheral blood sample is heparinized to prevent clotting, and the lymphocytes are separated by any known procedure for that purpose, such as the Ficoll-Hypaque gradient centrifugation method. See in this regard, Parish, C. R. & Hayward, T. A., *Proc. R. Soc. London Ser. B* 187:65–81 (1974) and Boylum, A., *Scand J. Clin. Lab. Ivest.*, Suppl 97, 21:77–78 (1968), the methods and procedures thereof being incorporated herein by reference. The mononuclear cell fraction is then washed and suspended in appropriate tissue culture fluid containing a suboptimally diluted polyclonal lymphocyte activator plus a nontoxic dilution of a specific antigen. The lymphocytes are cultured for 5 to 10 days, cells are harvested from the tissue culture and layered over Ficoll-Hypaque gradient to remove dead cells and debris and then the live cell fraction is washed with tissue culture fluid. The cells are counted because contrary to prior procedures (which use an excess of lymphocytes), it is preferred in the present procedure to fuse on a one-to-one ratio of tumor cells to lymphocytes.

As indicated above, the tumor cells do not have to be selectable in HAT medium or in any other medium used to select the fused cells from an overgrowth of tumor parent cells; the present procedure is sufficiently efficient that such a selective procedure may be avoided. Accordingly, there is a wide variety of tumor cells that are available for use in the present procedure which meet the other requirements that are necessary, namely, that the tumor cell does not secrete infectious virus and that it does not secrete the target protein, preferably no immunoglobulin. Such a tumor line is WIL2-NS, Accession No. ATCC CRL 8155, a non-secreting variant of WIL2 described in "Human Lymphoblastoid Lines from Lymph Node and Spleen", J. A. Levy, M. Virohainen, V. Defendi, *Cancer*, 22:517–524 (September 1958) incorporated herein by reference. Other lines are CCRF-SB, Accession No. ATCC CCL 120, a non-secreting mutant of RPMI 8226 and Raji, Accession No. ATCC CCL 86. Accordingly, one can use tumor cells that either are non-secreting mutants (U. W. Pickering and F. B. Gelder, *J. Immunol.*, 129:406–12 (1982)—azaguanine-resistant), or are not HGPRT or TK negative. The tumor cells are preferably in a log phase of growth when used for fusion. Thus, the majority of cells in the culture are actively dividing and metabolizing nutrients. A quick estimate of log phase growth may be obtained by comparing numbers of live versus dead cells in the culture. Log phase cultures have close to 100% viability. After harvesting cells from the tissue culture flask and washing them with tissue culture fluid, the tumor cells are counted.

The fusion procedure is started by mixing tumor cells and lymphocytes together at the preferred 1:1 ratio. At this point, the first stage in the present procedure is accomplished, namely, removing divalent ions from the cell environment. In one embodiment, this is accomplished by adding to the fusion mixture a solution of chelating agent. Alternatively, calcium and magnesium may be substantially removed by repeatedly washing the cells in the fusion mixture with calcium and magnesium-free medium, i.e., by repeated centrifugations and resuspensions in the described medium. When a chelating agent is used, preferably it is in a buffered saline solution. The agent can be any chelating agent useful for the removal of divalent ions so as to substantially remove all of the calcium and magnesium ions from the environment of the lymphocyte and tumor cell membranes, thereby destabilizing the cell membrane. Any of a variety of well known divalent ion chelating agents can be used, such as ethylene diamine tetraacetic acid (EDTA); ethylene glycol tetraacetic acid (EGTA); dithiothreitol; Dimercaprol or penicillamine. The chelating agent is added in a phosphate-buffered saline solution so that the pH of the solution preferably can be maintained in the physiological range of pH 7.0–7.5. Chelation is continued with repeated washing and decanting to finally obtain a cell pellet.

Next, as a second stage in the present procedure, a fusogen, i.e., an agent to facilitate fusion of the cells, is added. The agent should have little or no toxicity. Thus PEG is preferably not used. One can use a sterol such as cholesterol or lanosterol, or one can use a phosphoglyceride. For example, a phosphoglyceride micelle can be added to the pellet of destabilized tumor and lymphocyte cells. Preferably the phosphoglyceride is added in a solution of the chelating agent if that is used to destabilize the cells. The phosphoglyceride can, generally, be any of a variety of phosphorous containing lipid compounds which can form lipid bridges between the destabilized cells. Such phosphoglycerides include the phospholipids, compounds derived from the phosphoric ester of glycerol in which one of the primary hydroxyl groups of glycerol is esterified to phosphoric acid, and the other hydroxyl groups are esterified to fatty acids. Examples are phosphatidylethanolamine, phosphatidylcholine, phosphatidylserine, phosphatidylinositol and phosphatidylglycerol. The phosphoglycerides also include sphingolipids which also contain phosphorous and, like the phospholipids, are an important component of membranes. The backbone structure to which the fatty acids are attached in sphingolipids is sphingosine or a related base. Examples are sphingomyelin, cerebrosides and gangliosides. The phosphoglycerides are commercially available, some of which come in a liquid form in vials containing chloroform which must be evaporated before use. This can be accomplished by drying the phosphoglyceride in a glass tube with gaseous nitrogen and a sterile pasteur pipette. A suspension of the phosphoglyceride micelles in solution is added to the cell pellet to form a suspension maintained together for a short period of time.

As a third stage in the present procedure, polyvalent cations, preferably the calcium ions, and preferably also the magnesium ions, are slowly added back to the system. This is conveniently accomplished by diluting out the fusogen by the slow addition of tissue culture solution, which contains calcium and magnesium ions. One could use any of the standard tissue culture solutions, such as Roswell Park Memorial Institute (RPMI) 1640 solution, Eagle's minimum essential medium (MEM) or Dulbecco's Modified Eagle's Medium (DMEM). Thereafter, the cell pellet is resuspended in a desired complete tissue culture medium, such as the RPMI 1640 supplemented with a bactericide such as pen-strep bactericide and other growth supplements, such as immunoglobulin-free fetal calf serum. While great advantage of the present invention is the fact that the tumor cell line need not be HAT sensitive, nevertheless if a HAT sensitive tumor line is used, then HAT medium may be used for culture. However, HAT medium is not necessary in the present system and any complete medium that the tumor line grows well in will be appropriate.

When observed after as short a time period as 24 hours, hybridized cells are found that are viable and rapidly dividing. In contrast, cultures of cells fused using the standard PEG protocol show many dead cells at 24 hours; viable cells generally do not begin dividing until approximately 48 hours after fusion. With the present procedure, cell growth is sufficient within 3 to 5 days to test the supernatant fluid from the well for the presence of immunoglobulin. As soon as these tests are positive, the positive wells are cloned to separate antibody-secreting hybrids from unfused tumor cells. Because of the highly efficient nature of the present procedure, with an extremely rapid growth of hybrid cells, the hybridized cells are not overgrown by unfused tumor cells. Therefore one is able to separate the hybridized cells from the tumor cells present in the same cultures by limiting dilution cloning within one week of the fusion procedure. After selecting positive clones, one can proceed using standard monoclonal antibody production techniques to maintain the hybridoma culture.

Although hybridomas furnish a means of immortalizing the cells which produce desired endogenous proteins, the use of hybridomas is not without its disadvantages. For instance, certain human hybrid lines may be characterized by instability due to the extensive chromosome rearrangement and expulsion of chromosomes carrying antibody genes. Transfer of a limited number of chromosomes into a tumor cell, on the other hand, may increase the stability of the hybrid line because of there being fewer chromosomes involved in the cell hybridization requiring rearrangement. Thus where transfer of a complete new genome may result in rearrangement to the extent that antibody genes are lost, transfer of a limited number of extra chromosomes may obviate this problem.

The transfer of the genetic component of one cell into another cell has been described. For example, the fusion of mouse L-cell nuclei with human HeLa cells using Sendai virus as a fusogen is described in K. K. Sethi, et al., "Introduction of Mouse L Cell Nucleus Into Heterologous Mammalian Cells", Nature, 250:225–226 (1974). The mouse L-cell nuclei were obtained by treating the cells with cytochalasin B and introduced into enucleated human HeLa cells with the aid of inactivated Sendai virus. The presence of L-cell membrane properties on the cell surface of heterokaryons resulting from the fusion evidenced the effective functioning of the introduced L-cell nucleus.

The introduction into Chinese hamster ovary cells of chicken erythrocyte nuclei entrapped in phospholipid liposomes was reported in E. Kondorosi et al., "Introduction of Foreign Genetic Material Into Cultured Mammalian Cells by Liposomes Loaded with Isolated Nuclei", FEBS Lett. 120:37–40 (1980). Fusion of the nuclei loaded liposomes with the Chinese hamster ovary cells was spontaneous. The entrapped nuclei were found to retain at least part of their biological activity.

The fusion of mouse L-cell cytoplasts and karyoplasts from the A9 line of strain L929 mouse cells was reported in J. J. Lucs and J. R. Kates, "Nuclear Transplantation with Mammalian Cells", Chapter 20, p. 359–370. Enucleation was accomplished by means of cytochalasin B. Virus-mediated fusion of cytoplasts and karyoplasts resulted in reconstructed or hybrid cells which were found to be viable to the extent of at least 30%.

A. B. Mukherjee et al., "Entrapment of Metaphase Chromosomes into Phospholipid Vesicles (Lipochromosomes): Carrier Potential in Gene Transfer", Proc. Natl. Acad. Sci. USA, 75:1361–1365 (1978) describes the fusion of lipochromosomes to fibroblast cells. The lipochromosomes were prepared by treating fibroblast cells in the logarithmic phase of growth with Colcemid to block the cells in the mataphase stage, isolating the chromosomes by disruption of the cells and encapsulation of the chromosomes in a mixture of egg lecithin and cholesterol. Fusion was accomplished spontaneously in some instances and in other instances with the use of polyethylene glycol.

Several investigators have reported the transfer of individual chromosomes or groups of chromosomes. C.

A. McNeill et al., in "Genetic Manipulation by Means of Microcell-Mediated Transfer of Normal Human Chromosomes into Recipient Mouse Cells", *Proc. Natl. Acad. Sci. USA*, 77:5394–5398 (1980) disclosed the transfer of a single intact human chromosome into a mouse cell by using high concentrations of Colcemid to produce micronuclei in normal diploid human fibroblasts, enucleating the micronucleated cells with cytochalasin B and fusing the isolated microcells into recipient mouse cells by means of polyethylene glycol and phytohemagglutinin-P.

A. Tourian et al. in "Transfer of Human Chromosomes Via Human Minisegregant Cells into Mouse Cells and the Quantitation of the Expression of Hypoxanthine Phosphoribosyltransferase in the Hybrids", *J. Cell Sci.*, 30:193–209 (1978) described the fusion of micronuclei from human HeLa cells with whole malignant mouse fibroblasts using Sendai virus. The micronuclei are obtained by perturbing cell division in HeLa and diploid human cells to subdivide the mitotic cell into a cluster of minisegregants varying in size and DNA content. Enzyme activity of the HeLa parent was observed in hypoxanthine phosphoribosyl transferase deficient mouse cells.

R. E. K. Fournier in "A General High-Efficiency Procedure for Production of Microcell Hybrids", *Proc. Natl. Acad. Sci. USA*, 78:6349–6353 (1981) described microcell hybridization using polyethylene glyol and phytohemagglutinin-P in the fusion of the microcells to the intact recipient cells. Micronucleation is accomplished using sequential treatment of the donor cells with Colcemid and Cytochalasin B. The microcell hybrids resulting from this treatment may contain only a single donor derived chromosome or a small number of such chromosomes.

While the various hybridization techniques disclosed in the references cited above may provide useful tools for the study of the genetic makeup of various cells, for example, in gene mapping, the practical utilization of these methods has not been realized because the hybrids do not display sufficient stability to enable their long-term use. In particular, human hybrid lines have been characterized by marked instability.

The foregoing disadvantages may be overcome by a process which can be characterized as microcell "transertion". The process of transertion can be defined as the process of inserting into a tumor cell one or more chromosomes surrounded by nuclear membrane material from cells other than tumor cells. The resulting microcell transerted tumor cells have phenotypes of both the parent tumor cells, principally immortality, that is, the capacity to reproduce an almost limitless number of generations of cells, as well as phenotypes of the cells from which the microcells are derived, principally the ability to produce an endogenous protein which the tumor cells are incapable of producing.

The microcell transerted tumor cells are prepared in vitro by a process similar to that described above with respect to the fusion of tumor cells and cells capable of producing a desired endogenous protein. This process comprises the steps of substantially removing at least calcium ions from a culture of tumor cells which do not secrete desired proteins such as antibodies, interferons, lymphokines, hormone precursors or hormones, to destabilize the tumor cell membranes, mixing together (a) the destabilized tumor cells; (b) microcells comprising at least one chromosome surrounded by nuclear membrane material derived from mammalian eucaryotic cells which are capable of secreting such protein; and (c) a fusogen, adding back at least polyvalent cations to the resulting microcell transerted tumor cells and reproducing the microcell transerted tumor cells.

The process results in a tumor cell having from one to ten microcells transerted therein and possessing the characteristic immortality of the tumor cells and the endogenous protein producing capability of the cells from which the microcells are derived.

The procedure of the present invention is efficient and quick, resulting in viable and rapidly dividing microcell transerted tumor cells after as short a period as 24 hours.

The microcell transerted tumor cells can readily be separated from tumor cells present in the same cultures by a limiting dilution cloning using known tissue culture techniques, that is, by diluting the cultures to a concentration allowing theoretical distribution of one cell per tissue culture well. All cells subsequently arising in that well have the same parent and will be genetically identical.

The detailed transertion procedure will now be described. Following heparinizing of the peripheral blood sample, for example, and separation of lymphocytes and lymphocyte stimulation to increase the likelihood of transertion of microcells of specific protein-secreting cells into tumor cells, the cells are cultured. Culture of the cells in vitro is accomplished by incubating the cell suspension at 37 degrees Celsius in a 5% carbon dioxide:95% air mixture for about 5–10 days.

Harvest of the cells can be accomplished in a number of different ways. For example, the cultured lymphocyte suspension can be harvested by gentle pipetting and purified of dead cells and debris by Ficoll-Hypaque density gradient centrifugation. The live cell fraction is then washed with tissue culture medium and the cells are counted.

Alternatively, antigen-specific cells can be selected by a "panning" technique in which a plastic Petri dish is coated with specific antigen diluted in phosphate buffered saline (PBS) and incubated overnight at about 4 degrees Celsius. After incubation the antigen solution is decanted out of the dish, the dish is washed three times with PBS and the cultured lymphocyte cell suspension is harvested by gentle pipetting. The cells are then spun out of the culture medium by centrifugation at 500 rpm for 5 minutes, resuspended in culture medium lacking fetal bovine serum and transferred to the antigen-coated plate. The plate containing the cell suspension is then incubated at about 37 degrees Celsius for 30 minutes to 2 hours, after which non-adherent cells are removed by gentle pipetting, and the plate is washed two times with warm culture medium. Adherent cells, principally antigen-specific lymphocytes, are removed from the Petri dish by one of several methods. Adding cold ethylene glycol tetraacetic acid-phosphate buffered saline (EGTA-PBS) to the Petri dish and incubating the dish at 4 degrees Celsius for about 5 minutes is frequently adequate to remove adherent cells. However, those cells which remain adherent after incubation may be subjected to vigorous pipetting. As a last resort, the cells can be physically scraped from the dish using a sterile rubber policeman. Alternatively, the adherent cells may be left in the Petri dish and resuspended in RPMI plus 10% fetal bovine serum plus antibiotics at a cell concentration of 1 to 5 million cells per milliliter.

The resuspended cells are then subjected to a treatment to block the cells in the metaphase stage of the cell cycle. For this purpose Colcemid or Colchicine may be used. Colcemid, for example, may be added to a final concentration of 0.02 microgram per milliliter. The cell suspension is incubated at 37 degrees Celsius in an atmosphere of 5% carbon dioxide: 95% air for 15-20 hours.

The next step following metaphase blocking is disrupting the nuclear membrane and forming "microcells" containing a small number of individual chromosomes, usually 1-10 chromosomes. Microcell formation is accomplished by spinning the metaphase blocked lymphocytes out of the culture medium following the incubation period and resuspending the separated lymphocytes in RPMI plus 10% fetal bovine serum containing 10 micrograms per milliliter of Cytochalasin B.

Upon treatment of the metaphase blocked cells with Cytochalasin B or other drug capable of causing disruption of the nuclear membrane, the membrane disrupts and reforms around small numbers of individual chromosomes. Treatment consists of incubation for about 4 hours at 37 degrees Celsius in an atmosphere of 5% carbon dioxide:95% air.

The next step in the process is extrusion of the microcells through the cell membrane and pelleting of the microcells. The cell suspension, following incubation with Cytochalasin B or other suitable drug, is transferred to test tubes and subjected to ultracentrifugation at $28,000-29,000 \times g$ for about 30 minutes at 31-33 degrees Celsius. Following centrifugation, the supernatant is decanted and the pellet resulting from the centrifugation is suspended in 3 mM EGTA-PGS. The ultracentrifugation step is then repeated. The resulting pellet can be resuspended in culture medium or a basic salt solution for conducting the transertion. However, it is preferred to resuspend the pellet in EGTA-PBS, because it has been found that resuspension of the pellet in EGTA-PBS results in a higher yield of antibody-secreting cells following transertion of the microcells into tumor cells. When the microcells were washed with serumless RPMI rather than EGTA-PBS, it was found that many fewer antibody-secreting lines resulted. Apparently, the EGTA-PBS increases the efficiency of fusion, resulting in higher numbers of antibody-secreting lines due to the removal of calcium ions and magnesium ions from the environment of the microcells and that of the tumor cells.

The next step in the process is the suspension of the microcells in a fusogen, which is similar to the procedure for fusing tumor cells and protein-producing cells described above. Following the second ultracentrifugation step, the supernatant is discarded and the microcell pellet is resuspended in 1.0 ml of a suitable fusogen. The function of the fusogen is to facilitate transertion of the microcells into the tumor cells.

The tumor cells are likewise pelleted prior to mixing with the microcell pellet. In preparing the tumor cells for transertion of microcells, it is necessary to destabilize the membranes of the tumor cells by substantially removing at least calcium ions from the culture of tumor cells as described above. Mixing of the tumor cells and the microcells is accomplished by passing the suspension of microcells in fusogen through a 0.45 micron filter into the tumor cells, which removes "large" microcells, thus limiting those involved in the transertion process to microcells containing approximately 1-10 chromosomes. An additional 1.0 ml of fusogen is added to the microcell-tumor cell mixture dropwise over a one minute period. The tube containing the mixture is gently shaken in a 37 degree Celsius water bath for one minute and 5 ml of serumless RPMI is added to the tube dropwise over a period of approximately 5 minutes. The cell suspension is centrifuged at 500 rpm for 5 minutes, after which the supernatant is decanted and the RPMI dilution and centrifugation steps are repeated one time. The resulting microcell transerted tumor cell pellet is resuspended in complete tissue culture medium, for example, RPMI plus 10% fetal bovine serum and antibiotics, and dispensed into a 96 cell microtiter plate in a cell concentration of approximately $1-5 \times 10^5$ cells per ml.

The microtiter plate was found to contain antibody-secreting cells in as many as 50% of the wells. For example, human IgG antibody was detectable in the culture supernatants of cultures which were selected, cloned and carried in continuous culture for up to five months. In another case, anti-mouse F(ab) antibody was detected in microcell transerted tumor cells in which the lymphocytes had been stimulated with a specific antigen, the F(ab)'2 fragment of mouse IgG.

By using three times as many lymphocytes for microcell preparation as tumor cells, it has been foun that approximately one to ten microcells are transerted per tumor cell.

The final step in the process of the present invention is reproducing the microcell transerted tumor cells. For this purpose, cloning by both limiting dilutions and in soft agar were found effective. Soft agar cloning has the advantage of permitting visual observation of growing cell colonies and positive identification of those derived from a single cell. Limiting dilutions, on the other hand, is faster as well as being useful for cell lines which do not grow well in soft agar. Large numbers of antibody-secreting cell lines can be repetitively obtained by using the process of the present invention.

It will be appreciated that the present method proceeds by techniques and mechanisms that are distinct from prior techniques and mechanisms for transferring chromosomes to tumor cells, that is, for transerting microcells containing from one to ten chromosomes into tumor cells.

The invention will be better understood by reference to the following examples which are intended for purposes of illustration and are not to be construed as in any way limiting the scope of the present invention, which is defined in the claims appended hereto.

EXAMPLE I

Human peripheral blood from a patient suffering from systemic lupus erythematosis was heparinized to prevent clotting and the lymphocytes separated by Ficoll-Hypaque gradient centrifugation. The mononucler cell fraction was washed and suspended in RPMI 1640 tissue culture solution supplemented by pen-step bactericide, two millimoles of glutamine (an essential nutrient), $5 \times 10^5$ moles of 2-mercaptoethanol serving to enhance antigenic response (the mechanism of this action is poorly understood but the effect is well known, Goodman, M. D. and Weigle, W. O., J. Immunol. 120:1453 (1978)) and 10% calf serum at $5 \times 10^6$ cells per milliliter, and placed in tissue culture flasks. The cells were stimulated with a suboptimal dilution (i.e., a dilution determined in assays of cell proliferation to be less than that required for inducing maximal cell division but still allowing in vitro antibody production) of pokeweed mitogen from Gibco (1:400 final concentration) as a polyclonal stimulant. A 1:32 dilution of 18 mg/ml protein-containing crude preparation of extractable nuclear antigen obtained from a rabbit thymus extract by a method of Kurata and Tan, *Arth. Rheum.* 19:574 (1976) was added to the cell culture. The lymphocytes were thus cultured for about 6 days in a humidified incubator at 37 degrees Celsius, in an atmosphere containing 5% carbon dioxide. Thereafter, cells were harvested from the tissue culture flask and layered over Ficoll-Hypaque gradient to remove dead cells and debris. A live cell fraction was obtained which was washed with RPMI 1640 (no serum) and counted. A total number of $2 \times 10^6$ cells was obtained.

As tumor cells, cells from a human lymphoblastoid cell line, established from the spleen of a patient having hereditary spherocytic anemia, were used, and these were obtained under the designation WIL2-NS human lymphoblastoid cell line, Accession No. ATCC-CRL 8155. This cell line does not secrete immunoglobulin nor does it secrete infectious virus, and it is not HGPRT or TK enzyme negative. The tumor cells were harvested from tissue culture flasks while in the log phase of growth, as indicated by cell viability of close to 100% in tissue culture flasks. The tumor cells were washed with RPMI 1640 (no serum) and $2 \times 10^6$ cells were counted.

The tumor cells and lymphocytes were mixed together at a 1:1 cell ratio in a round-bottomed tube. The cell mixture was spun gently at about 500 rpm for about 5 minutes, bringing about cell contact. The tube was then left undisturbed in the $CO_2$ incubator for about 60 minutes. Thereafter, the cells were again spun gently and the culture medium decanted. A solution of calcium-magnesium-free phosphate-buffered (to pH 7.4) saline solution containing 3 millimolar EGTA, at 37 degrees Celsius, was added to the cells to remove all calcium and magnesium ions from the cell environment, thus destabilizing the cell membranes. The cells were gently spun and supernatant decanted, washed with the calcium-magnesium-free chelating solution, spinning and decanting being repeated two more times. The tube containing the cell pellet was then placed into a beaker of water at 37 degrees Celsius. A 10 mg % solution of lysophosphatidylethanolamine in the EGTA-phosphate buffered saline solution was prepared. The final solution was vortexed very vigorously to suspend the phospholipid micelles and was then added dropwise over a period of about 45–60 seconds to the cell pellet obtained above. The cells plus the phospholipid solution were left undisturbed in the 37 degree Celsius water bath for 60 seconds. Thereafter, RPMI 1640 (no serum) at 37 degrees Celsius was added dropwise over a period of several minutes to dilute out the chelating agent and to slowly add calcium and magnesium ions back to the system. The cells were then spun down very gently and the supernatant decanted. RPMI 1640 (no serum) was again added and the cells were again spun down. The cell pellet was then resuspended in a complete tissue culture medium formed of RPMI 1640, pen-strep bactericide, glutamine, and fetal calf serum, described above. The tissue culture was dispensed in 0.1 ml volumes ($2.5 \times 10^5 - 5 \times 10^5$ cells/0.1 ml) into round-bottom microtiter wells. The next day an additional 0.1 ml of complete tissue culture medium was added. In about 2 days, the tissue culture medium was found to be acidic and a good cell pellet was visible. Wells were assayed for presence of human immunoglobulin. Positive wells were then immediately cloned. Afer selecting clones, positive for anti-rabbit thymus extract antibody secretion, standard monoclonal antibody production techniques were used to maintain the tissue culture. Thus, selected clones were expanded by transferring the cultures to increasingly larger tissue culture containers with fresh culture medium as the cells continued to divide. Specific antibody secretion was assayed repeatedly to check stability of the antibody-secreting lines.

Following this procedure, ten cloned, monoclonal hybridoma lines have been selected for long term maintenance with aliquots of cells being stored in liquid nitrogen. All of the lines grow rapidly and secrete IgG or IgM antibodies only. Antibody specificity was determined using an enzyme-linked immunosorbent assay system. Four of the lines reacted with rabbit thymus extract antigens only, five reacted with the rabbit thymus extract antigens and cross-reacted with native DNA. One line reacted with rabbit thymus extract and heat-inactivated rabbit thymus extract (possibly indicating reactivity with the heat-stable antigen designated Sm), and one line reacted with rabbit thymus extract and heat-inactivated rabbit thymus extract, as well as cross-reacting with native DNA. An additional line was not apparently monoclonal, as both IgG and IgM were secreted, the antibodies reacting most strongly with native DNA, but also reacting with rabbit thymus extract. No reactivity of this line with heat-inactivated rabbit thymus extract was apparent.

Figure 2:
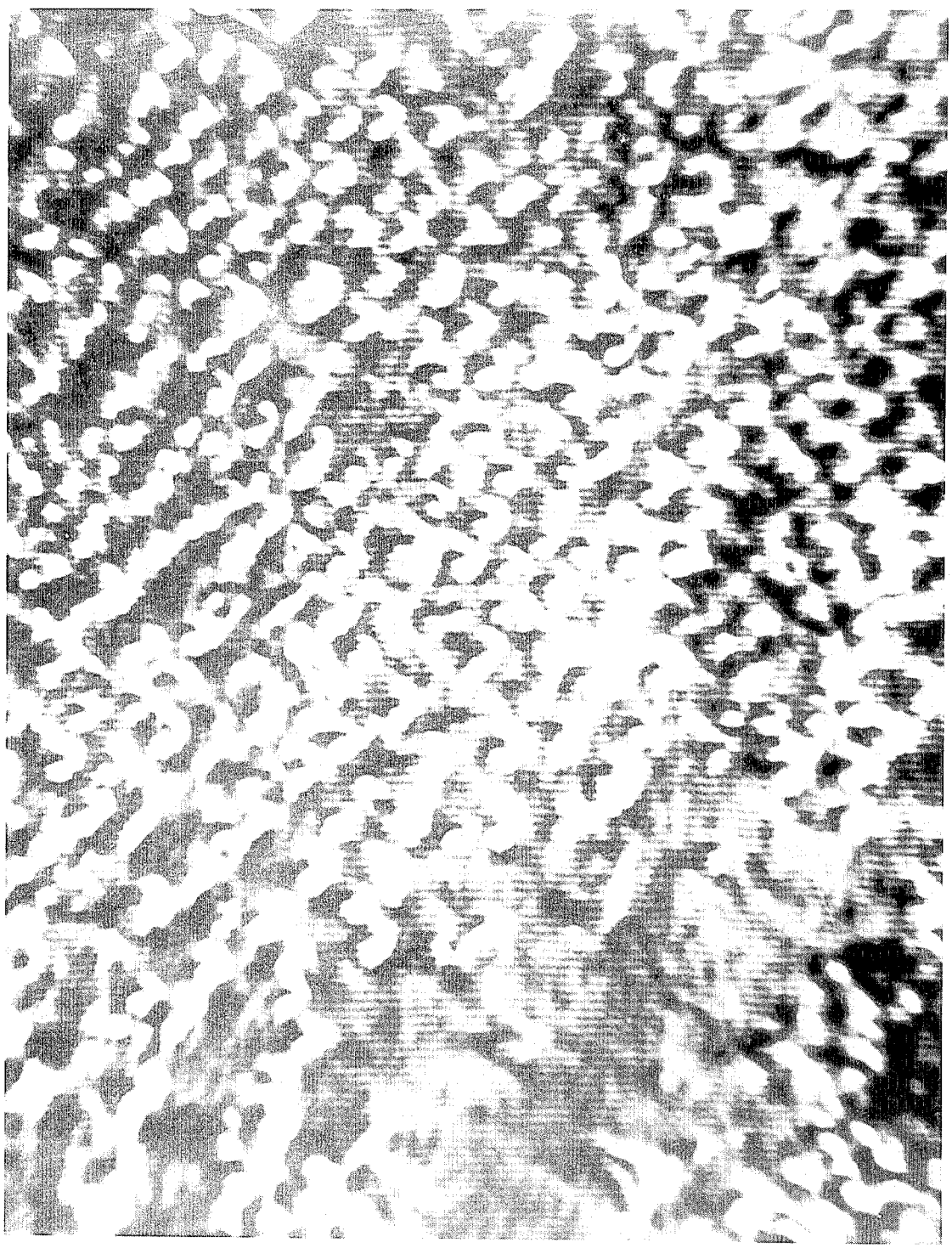
FIG. 2 is a photograph at 100× magnification of cells from a microtiter well from an experiment performed on the same day as the experiment which yielded the cells of FIG. 1, also photographed 18 hours after fusion but prepared in accordance with the present invention.

Referring now to FIG. 1, there is shown a view magnified 100 times of cells in a microtiter well 18 hours after a standard PEG fusion procedure was conducted. Very few cells are present, most of which are opaque, indicating cell death. This is a typical appearance of cultures for a period of 48 hours after fusion with PEG. Healthy colonies visible with the naked eye are generally not observable for 10–14 days and sometimes not for up to four weeks. Referring to FIG. 2, there is shown a view of cells magnified 100 times from the foregoing Example 1, performed on the same day as the experiment yielding the cells of FIG. 1, and also photographed 18 hours after fusion. A large number of cells are observed growing in colony formation. The bright appearance of the cells indicates that they are alive and healthy. These cultures had outgrown the small wells by 48 hours and were ready for transfer to larger containers.

EXAMPLE II

The procedure of Example I was followed except that in place of peripheral blood lymphocytes from a patient suffering from SLE, the lymphocytes were obtained from the peripheral blood of a normal human donor. As antigen, the lymphocytes were stimulated in vitro with sheep red blood cells and the polyclonal stimulant pokeweed mitogen. In addition to lysophosphatidylethanolamine as a fusogen, phosphatidylethanolamine, phosphatidylcholine and lysophosphatidylcholine were used. Antibody-secreting hybrids were obtained with all fusogens except lysophosphatidylcholine. Sixteen lines were selected producing either IgM or IgG antibody specific for sheep red blood cells.

EXAMPLE III

The procedure of Example II was followed except that the normal lymphocytes were stimulated in vitro with the mouse antibody subclass IgG2a in the form of culture supernatant from a mouse myeloma line secreting IgG2a antibody plus lipopolysaccharide as a polyclonal stimulant. Phosphatidylethanolamine and phosphatidylcholine were used as fusogens. Following this procedure, four cloned lines were selected, producing specific anti-mouse-IgG antibody.

EXAMPLES IV-V

The procedure of Example I was followed except that the donor lymphocytes were stimulated in vitro with either lipopolysaccharide alone or in combination with purified DNA. Fusogens were the same as in Example III. Two groups of lines were produced showing monoclonal antibody activity against extractable nuclear antigens and/or DNA.

EXAMPLE VI

The procedure of Example I was followed except as described herein to produce human antineuroblastoma antibodies. Biopsy material from a human neuroblastoma tumor was placed into in vitro culture by preparing a single cell suspension of the tumor which was maintained in RPMI 1640 tissue culture medium supplemented with 10% fetal calf serum. These tumor cells were used as an antigen, along with pokeweed mitogen, to stimulate normal human peripheral blood lymphocytes in vitro for five days. Stimulated lymphocytes were fused with WIL2-NS human lymphoblastoid tumor cells following the protocols described, and using phosphatidylcholine as the fusogen. Antibodies specifically binding to the surface of the neuroblastoma cells were detected using an ELISA assay.

One can utilize the foregoing procedures, as indicated previously, to fuse cell lines other than those producing antibodies. Thus, following the procedure of Example I, one can substitute the tissue cultures indicated in Examples VII-X for the antibody-secreting lymphocytes.

EXAMPLE VII

Human thyroid follicular cells can be fused with tissue culture adapted thyroid tumor cells or non-immunoglobulin-secreting lymphoid tumor lines to yield a hybridoma which will secrete thyroid hormones. As a model system, thyroid follicular cells obtained from mice were fused with a HAT-sensitive mouse myeloma cell line designated Sp2/0, Shulman, M., C. D. Wilde, G. Kohler, "A Better Cell Line for Making Hybridomas Secreting Specific Antibodies", *Nature* 276:269 (1978). Mouse thyroids were aseptically removed, follicular cell suspensions obtained by treating the tissue with collagenase, and cell suspensions placed into in vitro culture in medium containing thyroid stimulating hormone to induce production of thyroid hormones. Cell monolayers were removed from tissue culture wells with trypsin and were fused at 1:1 ratio with the mouse tumo cells following the procedure described in Example I, except that phosphatidylcholine was used as the fusogen. After suitable cell growth had occurred, as evidenced by increased cell numbers and an acidic pH change in the medium, cell culture supernatants were assayed for the presence of thyroxin (T4) by an enzyme-linked immunosorbent assay and by a clinical radioimmunoassay. Two lines were selected for long-term maintenance and cloning.

This procedure has also been completed using human thyroid cells from thyroids obtained at surgery. The procedure is exactly the same except that a HGPRT or TK enzyme negative WIL2-S human lymphoblastoid cell line, Accession No. ATCC-CRL 8885 was used as the tumor line. Ten cloned lines were selected.

EXAMPLE VIII

Human pituitary cells can be used to yield a hybridoma which will secrete growth hormone. Normal human pituitary cells were obtained from a pituitary obtained at autopsy performed immediately following death. Single cell suspensions were obtained from the tissue by collagenase treatment and were further purified by Percoll density gradient separation. These cells were placed into in vitro culture for 48 hours prior to fusion. The fusion procedure described in Example I, with the exception that phosphatidylcholine was used as the fusogen, was followed to fuse the pituitary cells with the human B cell tumor line WIL2-NS. An enzyme-linked immunosorbent assay system can be used to select hybrid lines capable of secreting human growth hormone into the culture medium.

EXAMPLE IX

Human fibroblasts and/or human thymus-derived (T) lymphocytes can be used to yield a hybridoma which secretes interferon. Human peripheral blood lymphocytes were obtained from a healthy normal donor. These cells were cultured in vitro with a concentration of Concanavalin A (a plant lectin) determined to be stimulatory for production of gamma interferon. After 72 hours the "stimulated" lymphocytes were fused at a 1:1 ratio with the human B cell tumor line WIL2-NS following the procedure described in Example I except that the fusogen was phosphatidylcholine. After five days in culture, supernatant medium from the hybrid cells was assayed for the presence of interferon-like activity by a viral-inhibition assay system. Thirteen cell lines selected for interferon-like secretion have been maintained in culture and/or stored in aliquots in liquid nitrogen.

EXAMPLE X

Human thymus-derived (T) lymphocytes or macrophages can be used to yield various lymphokines. Production of various lymphokines such as interleukin II or macrophage inhibiting factor can be achieved in the manner described for interferon in Example IX. Thus, peripheral blood lymphocytes from normal human donors can be stimulated in vitro with concentrations of mitogens (for example, Concanavalin A) suitable for inducing production of the lymphokine. After this induction phase, the lymphocytes can be fused, following the procedure described in Example I, to a human lymphocyte tumor, and hybrid lines can be selected on the basis of lymphokine presence in the culture supernatants.

EXAMPLE XI

As stated above, one can use the procedures presented herein to fuse tumor cells from one species with lymphocytes from another species. Spleen and peripheral blood lymphocytes from an Aotus monkey infected with malaria parasites were fused, using the procedure of Example I, with the WIL2-NS human tumor line. Prior to fusion, the monkey lymphocytes were stimulated in vitro with pokeweed mitogen and malaria parasites in order to induce blastogenesis and expand clones of antigen-specific lymphocytes. The products of this fusion were determined by an ELISA assay and immunofluorescence to be producing antibodies which bound specifically to malaria parasites.

EXAMPLE XII

Sterols such as cholesterol can be used in place of phospholipids. Following the procedure of Example III, in which human monoclonal antibodies are produced against mouse IgG, peripheral blood lymphocytes from a normal human donor can be stimulated in vitro with pokeweed mitogen and mouse IgG for five days. After five days, the stimulated normal lymphocytes can be fused with the WIL2-NS human lymphoblastoid tumor line using the protocols described with the exception that cholesterol or other sterol compounds can be used in place of a phospholipid as the fusogen. Procedures for culturing hybridomas and assaying for antibody specificity would remain the same.

EXAMPLES XIII–XVI

To illustrate the use of tumor lines that secrete antibody (in place of tumor lines that are non-secreting), the procedure of Example I can be followed substituting for the WIL-2-NS human lymphoblastoid line, one of the following:

P3X63Ag8, the original mouse line used by Kohler and Milstein which secretes whole IgG (G. Kohler, C. Milstein, "Derivation of Specific Antibody-producing Tissue Culture and Tumor Lines by Cell Fusion", *Eur. J. Immunol.*, 6:511 (1976)).

a derivative of the above line—NS2 (NS2-AG4-2)—which secretes light chains only (Kohler, G., S. C. Howe, C. Milstein, "Fusion Between Immunoglobulin Secreting and Nonsecreting Lines", *Eur. J. Immunol.*, 6:292 (1976)).

The Stanford human line—SKO 007—which secretes IgE (Olsson, L., H. S. Kaplan, "Human-human Hybridomas Producing Monoclonal Antibodies of Predefined Specificity", *Proc. Natl. Acad. Sci. USA*, 77:5429 (1980)).

The Croce human line—GM-1500-6TG—which secretes IgG (Croce, C. M. A. Linnenbach, W. Hall, Z. Steplewski, H. Koprowski, "Production of Human Hybridomas Secreting Antibodies to Measles Virus", *Nature*, 288:488 (1980)).

Non-specific antibody produced by hybrids obtained from fusions of antibody-secreting tumor cells with normal lymphocytes can be separated from the antigen-specific antibody by passing antibody-containing ascites fluid or culture supernatants over an immunoadsorbent column prepared by attaching the specific antigen to Sepharose using cyanogen bromide. Antigen-specific antibody will bind to the column, while non-specific antibody passes through and is discarded. Specific antibody may then be eluted from the column by lowering the pH of the column.

EXAMPLE XVII

It may be useful to fuse two tumor cells using the techniques described in this document. For example, cells from a patient's tumor, such as a lung carcinoma, can be taken at biopsy and fused with an established human lymphoid tumor line, such as WIL2-NS using the techniques described in Example I. These hybrids, once established, would be useful in testing the drug sensitivity of the patient's tumor, as a means of evaluating candidate chemotherapeutic regimens in vitro.

The use of microcells in preparing monoclonal antibody-producing fused cells is described in the following examples.

EXAMPLE XVIII

The procedure of Example III was followed except that microcells produced from peripheral blood lymphocytes obtained from a normal donor stimulated in vitro with the F(ab')2 fragment of mouse IgG and the WIL2-S cell line described in Example VII were used. Phosphatidylcholine was used as the fusogen. Cloned lines were selected producing antibody with specificity for the F(ab')2 fragment of mouse IgG.

EXAMPLE XIX

The procedure of Example III was followed except that microcells produced from peripheral blood lymphocytes obtained from a normal donor stimulated in vitro with pokeweed mitogen and the WIL2-S cell line were used. Phosphatidylcholine was used as the fusogen. Cloned lines were selected producing human antibody of IgG and IgM classes.

EXAMPLE XX

The procedure of Example III was followed except that microcells produced from peripheral blood lymphocytes obtained from a donor suffering from systemic lupus erythematosis stimulated by the beta subunit of human chorionic gonadotropin or the F(ab')2 fragment of mouse IgG and pokeweed mitogen and the HS Sultan human lymphoblastoid cell line, Accession No. ATCC-CRL 1484 were used. Phosphatidylcholine was used as the fusogen. Cloned lines were selected producing human antibody of IgG and IgM classes.

DEPOSITORY INFORMATION

Five lines have been described above by their American Type Culture Collection numbers. More specifc information with regard to the deposit of these lines is as follows: each of the lines is on deposit with the American Type Culture Collection at 12301 Parklawn Drive, Rockville, Md., 20852.

The WIL2-NS line has Accession No. ATCC-CRL 8155 given by that institution with a date of deposit of Aug. 6, 1982. The CCRF-SB line has Accession No. ATCC CCL 120 with a date of deposit of April, 1968. The Raji line has Accession No. ATCC CCL 86 with a date of deposit of March, 1967.

The WIL2-S line has Accession No. ATCC-CRL 8885 with a date of deposit of Aug. 15, 1985. The HS Sultan line has Accession No. ATCC-CRL 1484 with a date of deposit of November, 1982.

The antibodies, hormones, lymphokines and interferon have obvious and well known uses in the treatment of various diseases and disfunctions. The present process is particularly useful in making all of such materials more readily, efficiently and economically available. In addition, antibodies produced following Example I can be used to study the structure and function of extractable nuclear antigens and DNA. The diversity of auto-antibody reactions in SLE, for example, may be a result of a relatively simple antigenic structure in a variety of biological molecules.

The foregoing description of the invention has been directed to particular preferred embodiments for puposes of explanation and illustration. It will be apparent, however, to those skilled in the art, that many modifications and changes in the methods and materials may be made without departure from the scope and spirit of the invention. For example, other non-tumor cells than lymphocytes and other specific manipulations than those exemplified herein may be used. Particular antibodies and other biologically active compounds have been chosen for convenience and are not intended to limit the scope of this invention. It is the applicant's intention in the following claims to cover all such equivalent modifications and variations as fall within the true spirit and scope of the invention.

What is claimed is:

1. A process for the preparation of monoclonal antibody-producing hybridomas which comprises:
    mixing together in vitro
        (a) tumor cells from a WIL2-NS human lymphoblastoid cell line, Accession No. ATCC-CRL 8155, which do not secrete immunoglobulin or infectious virus; and
        (b) peripheral blood lymphocytes obtained from a donor suffering from systemic lupus erythematosis, cultured in vitro with rabbit thymus extract and a polyclonal lymphocyte activator selected from the group consisting of pokeweed mitogen and lipopolysaccharides;
    substantially removing at least calcium ions from the cell environment, whereby to destabilize the membranes of said cells;
    adding a fusogen selected from the group consisting of phosphoglycerides and sterols to said destabilized cells;
    diluting the mixture of fusogen and destabilized cells with tissue culturer medium containing polyvalent cations;
    whereby to obtain said hybridomas by fusion of said tumor cells and said lymphocytes; and
    separating and reproducing said hybridomas.

2. A process for the preparation of monoclonal antibody-producing hybridomas which comprises:
    mixing together in vitro
        (a) tumor cells from a WIL2-NS human lymphoblastoid cell line, Accession No. ATCC-CRL 8155, which do not secrete immunoglobulin or infectious virus; and
        (b) peripheral blood lymphocytes obtained from a normal donor, cultured in vitro with sheep red blood cells and pokeweed mitogen as a polyclonal stimulant;
    substantially removing at least calcium ions from the cell environment whereby to destabilize the membranes of said cells;
    adding a fusogen selected from the group consisting of phosphoglycerides and sterols to said destabilized cells;
    diluting the mixture of fusogen and destabilized cells with tissue culture medium containing polyvalent cations;
    whereby to obtain said hybridomas by fusion of said tumor cells and said lymphocytes; and
    separating and reproducing said hybridomas.

3. A process for the preparation of monoclonal antibody-producing hybridomas which comprises:
    mixing together in vitro
        (a) tumor cells from WIL2-NS human lymphoblastoid cell line, Accession No. ATCC-CRL 8155, which do not secrete immunoglobulin or infectious virus; and
        (b) peripheral blood lymphocytes obtained from a normal donor, cultured in vitro with culture supernatant from a mouse myeloma line secreting IgG2a antibody, and lipopolysaccharide as a polyclonal stimulant;
    substantially removing at least calcium ions from the cell environment, whereby to destabilize the membrane of said cells;
    adding a fusogen selected from the group consisting of phosphogylcerides and sterols to said destabilized cells;
    diluting the mixture of fusogen and destabilized cells with tissue culture medium containing polyvalent cations;
    whereby to obtain said hybridomas by fusion of said tumor cells and said lymphocytes; and
    separating and reproducing said hybridomas.

4. A process for the preparation of monoclonal antibody-producing hybrodimas which comprises:
    mixing together in vitro
        (a) tumor cells from a WIL2-NS human lymphbastoid cell line, Accession No. ATCC-CRL 8155, which do not secrete immunoglobulin or infectious virus; and
        (b) peripheral blood lymphocytes obtained from a donor suffereing from systemic lupus erythematosis, cultured in vitro with lipopolysaccharide as a polyclonal stimulant;
    substantially removing at least calcium ions from the cell environment, whereby to destabilize the membranes of said cells;
    adding a fusogen selected from the group consisting of phosphoglycerides and sterols to said destabilized cells;
    diluting the mixture of fusogen and destabilized cells with tissue culture medium containing polyvalent cations;
    whereby to obtain said hybridomas by fusion of said tumor cells and said lymphocytes; and
    separating and reproducing said hybridomas.

5. A process for the preparation of monoclonal antibody-producing hybridomas which comprises:
    mixing together in vitro
        (a) tumor cells from a WIL2-NS human lymphoblastoid cell line, Accession No. ATCC-CRL 8155, which do not secrete immunoglobulin or infectious virus; and
        (b) peripheral blood lymphocytes obtained from a donor suffereing from systemic lupus erythematosis, cultured in vitro with purified DNA and lipopolysaccharide as a polyclonal stimulant;
    substantially removing at least calcium ions from the cell environment to destabilize the membranes of said cells;
    adding a fusogen selected from the group consisting of phosphoglycerides and sterols to said destabilized cells;
    diluting the mixture of fusogen and destabilized cells with tissue culture medium containing polyvalent cations;
    whereby to obtain said hybridomas by fusion of said tumor cells and said lymphocytes; and
    separating and reproducing said hybridomas.

6. A process for the preparation of interferon-producing hybridomas which comprises:
    mixing together in vitro
        (a) tumor cells from a WIL2-NS human lymphoblastoid cell line, Accession No. ATCC-CRL 8155, which do not secrete immunoglobulin or infectious virus; and
        (b) peripheral blood lymphocytes obtained from a normal donor, cultured in vitro with Concanavalin A;

substantially removing at least calcium ions from the cell environment to destabilize the membranes of said cells;

adding a fusogen selected from the group consisting of phosphoglycerides and sterols to said destabilized cells;

diluting the mixture of fusogen and destabilized cells with tissue culture medium containing polyvalent cations;

whereby to obtain said hybridomas by fusion of said tumor cells and said lymphocytes; and separating and reproducing said hybridomas.

7. A process for the preparation of human growth hormone-producing hybridomas which comprises: mixing togehter in vitro (a) tumor cells from a WIL2-NS human lymphoblastoid cell line, Accession No. ATCC-CRL 8155, which do not secrete immunoglobulin or infectious virus; and (b) normal human pituitary cells, cultured in vitro;

substantially removing at least calcium ions from the cell environment to destabilize the membranes of said cells;

adding a fusogen selected from the group consisting of phosphoglycerides and sterols to said destabilized cells;

diluting the mixture f fusogen and destabilized cells with tissue culture medium containing polyvalent cations;

whereby to obtains aid hydridomas by fusion of said tumor cells and said lymphocytes; and separating and reproducing said hybridomas.

8. A process for the preparation of monoclonal antibody-producing hybridomas which comprises:

mixing together in vitro (a) tumor cells from a WIL2-NS human lymphoblastoid cell line, Accession No. ATCC-CRL 8155, which do not secrete immunoglobuline or infectious virus; and (b) peripheral blood lymphocytes obtained from a normal donor, cultured in vitro with human neuroblastoma bumor cells and pokeweed mitogen as a polyclonal stimulant;

substantially removing at least calcium ions from the cell environment to destabilize the membranes of said cells;

adding a fusogen selected from the group consisting of phosphoglycerides and sterols to said destabilized cells;

diluting the mixture of fusogne and destabilized cells with tissue culture medium containing polyvalent cations;

whereby to obtain said hybridomas by fusion of said tumor cells and said lymphocytes; and separating and reproducing said hybridomas.

9. A process for the preparation of monoclonal antibody-producing microcell transerted tumor cells which comprises:

substantially removing at least calcium ions from a culture of tumor cells from a WIL2-S human lymphoblastoid cell line, Accession No. ATCC-CRL 8885, which do not secrete immunoglobulin or infectious virus, whereby to destabilize the membranes of said tumor cells;

mixing together in vitro (a) the destabilized tumor cells;

(b) microcells comprising at lest one chromosome surrounded by nuclear membrane material derived from peripheral blood lymphocytes obtained from a normal donor, cultured in vitro with pokeweed mitogen as a polyclonal lymphocyte activator; and (c) a fusogen selected from the group consisting of phosphoglycerides and sterols;

whereby to transert said microcells into said tumor cells;

diluting the resulting microcell transerted tumor cells with tissue culture medium containing polyvalent cations; and separating and reproducing said microcell transerted tumor cells.

10. A process for the preparation of monoclonal antibody-producing microcell transerted tumor cells which comprises:

substantially removing at least calcium ions from a culture of tumor cells from a WIL2-S human lymphoblastoid cell line, Accession No. ATCC-CRL 8885, which do not secrete immunoglobulin or infectious virus, whereby to destabilize the membranes of said tumor cells;

mixing together in vitro (a) the destabilized tumor cells;

(b) microcells comprising at least one chromosome surrounded by nuclear membrane material derived from peripheral blood lymphocytes obtained from a normal donor, cultured in vitro with the F(ab')2 fragment of mouse IgG antibody and pokeweed mitogen as a polyclonal lymphocyte activator; and (c) a fusogen selected from the group consisting of phosphoglycerides and sterols;

whereby to transert said microcells into said tumor cells;

diluting the resulting microcell transerted tumor cells with tissue cultue medium containing polyvalent cations; and separating and reproducing said microcell transerted tumor cells.

11. A process for the preparation of monoclonal antibody-producing microcell transerted tumor cells which comprises:

substantially removing at least calcium ions from a culture of tumor cells from a HS Sultan human lymphoblastoid cell line, Accession No. ATCC-CRL 1484, which do not secrete immunoglobulin or infectious virus, whereby to destabilize the membranes of said tumor cells;

mixing together in vitro (a) the destabilized tumor cells;

(b) microcells comprising at least one chromosome surrounded by nuclear membrane material derived from peripheral blood lymphocytes obtained from a donor suffering from systemic lupus erythematosis, cultured in vitro with an antigen selected from the group consisting of the beta subunit of human chorionic gonadotropin and the F(ab')2 fragment of mouse IgG and pokeweed mitogen as a polyclonal lymphocyte activator; and (c) a fusogen selected from the group consisting of phosphoglycerides and sterols;

whereby to transert said microcells into said tumor cells;

diluting the resulting microcell transerted tumor cells with tissue culture medium containing polyvalent cations; and separating and reproducing said microcell transerted tumor cells.

* * * * *